(12) United States Patent
Li et al.

(10) Patent No.: US 12,222,329 B1
(45) Date of Patent: Feb. 11, 2025

(54) MESOMECHANICS TESTING SYSTEM AND METHOD INTEGRATING HEATING AND OBSERVATION

(71) Applicant: INSTITUTE OF GEOLOGY AND GEOPHYSICS, CAS, Beijing (CN)

(72) Inventors: Lihui Li, Beijing (CN); Beixiu Huang, Beijing (CN); Zhongming Du, Beijing (CN)

(73) Assignee: INSTITUTE OF GEOLOGY AND GEOPHYSICS, CAS, Beijing (CN)

( * ) Notice: Subject to any disclaimer, the term of this patent is extended or adjusted under 35 U.S.C. 154(b) by 0 days.

(21) Appl. No.: 18/773,909

(22) Filed: Jul. 16, 2024

(51) Int. Cl.
*G01N 3/18* (2006.01)
*G01N 3/06* (2006.01)
*G01N 33/24* (2006.01)

(52) U.S. Cl.
CPC .............. *G01N 3/18* (2013.01); *G01N 3/068* (2013.01); *G01N 33/24* (2013.01); *G01N 2203/0208* (2013.01); *G01N 2203/0226* (2013.01); *G01N 2203/0234* (2013.01); *G01N 2203/0647* (2013.01)

(58) Field of Classification Search
CPC .......... G01N 3/18; G01N 3/068; G01N 33/24; G01N 2203/0208; G01N 2203/0226; G01N 2203/0234; G01N 2203/0647
See application file for complete search history.

(56) References Cited

U.S. PATENT DOCUMENTS 11,041,383 B2 * 6/2021 Hao ..................... G01N 33/241

FOREIGN PATENT DOCUMENTS

| CN | 104913981 A | | 9/2015 | |
|---|---|---|---|---|
| CN | 105466778 A | | 4/2016 | |
| CN | 108760526 A | * | 11/2018 | ............... G01N 1/44 |
| CN | 114544654 A | * | 5/2022 | |
| CN | 116008131 A | * | 4/2023 | |

* cited by examiner

*Primary Examiner* — Octavia Hollington
(74) *Attorney, Agent, or Firm* — WC&F IP

(57) ABSTRACT

Provided are a mesomechanics testing system and method integrating heating and observation, relating to the field of rock mechanics testing. The system includes a control and collection module, a loading module, a vacuum module, and an observation module. The loading module and the observation module are both connected to the control and collection module; the loading module is configured to apply a load required by mechanics testing to a mesoscopic sample to be tested, and transmit mechanics testing data to the control and collection module; the vacuum module is configured to provide the mesoscopic sample with a vacuum space for real-time heating and mechanics testing; and the observation module is configured to collect image data of the mesoscopic sample during the mechanics testing, and transmit the image data to the control and collection module.

10 Claims, 4 Drawing Sheets

MESOMECHANICS TESTING SYSTEM AND METHOD INTEGRATING HEATING AND OBSERVATION

CROSS REFERENCE TO RELATED APPLICATION

This patent application claims the benefit and priority of Chinese Patent Application No. 202310896766.1, filed with the China National Intellectual Property Administration on Jul. 21, 2023, the disclosure of which is incorporated by reference herein in its entirety as part of the present application.

TECHNICAL FIELD

The present disclosure relates to the field of rock mechanics testing, and in particular, to a mesomechanics testing system and method integrating heating and observation.

BACKGROUND

With the continuous development of economies around the world, underground resources are gradually becoming the main force in the future energy structure. The engineering construction is also moving to fields in the deep earth, including underground projects such as geothermal energy exploitation, high-temperature water diversion tunnel construction, and ultra-deep well drilling. In these projects, the formation temperature is usually high, and the impact of the high-temperature environment on the physical and mechanical properties of rock materials has always been an inevitable problem in engineering practice.

In the underground projects, the formation temperatures at different depths or in different environments are different, and the mechanical parameters and deformation and failure laws of the corresponding rock materials are also different, which directly affect the construction safety and the construction progress. Previous researchers have conducted a lot of research on the physical and mechanical properties of the rock materials under different temperature conditions. However, due to the limitations of research technical means, the rock materials are usually first subjected to high-temperature treatment, and then conventional rock mechanics testing is carried out after the rock materials are cooled to room temperature. This rock mechanics testing method after high-temperature treatment may reflect the influence of the temperature on the mechanical properties of rock to a certain extent. However, because the effect of the cooling process on the mechanical properties of the rock cannot be eliminated, the acquired mechanical properties cannot represent the mechanical properties of the rock at the actual formation temperature. To solve such problems, some scholars have researched and developed a testing system that may perform mechanical loading at a real-time high temperature. However, the system usually lacks a matching synchronous observation module, such that it is impossible to synchronously observe the rock deformation and failure process, and it is difficult to reveal crack extension laws of the rock materials at a high temperature. In this regard, some scholars have tried to employ the CT scanning technology to acquire image data during the loading process. However, because the CT scanning is usually performed at a specified site and the scanning takes a certain amount of time, it is impossible to truly achieve synchronous observation of the deformation and failure process. In addition, the conventional rock mechanics testing requires the preparation of macro-scale standard samples, which is not applicable to rock materials with limited samples that do not meet standard mechanics testing requirements.

SUMMARY

An objective of the present disclosure is to provide a mesomechanics testing system and method integrating heating and observation, which can acquire the mechanical properties of mesoscopic samples to be tested at a real-time high temperature and simultaneously observe the crack extension process of the samples.

To achieve the above objective, the present disclosure provides the following solutions:

A mesomechanics testing system integrating heating and observation, where the system includes a control and collection module, a loading module, a vacuum module, and an observation module;

the loading module and the observation module are both connected to the control and collection module;

the vacuum module is configured to provide a mesoscopic sample to be tested with a vacuum space for real-time heating and mechanics testing;

the loading module is configured to apply a load required by the mechanics testing to the mesoscopic sample in the vacuum space, and transmit mechanics testing data to the control and collection module; and the observation module is configured to collect image data of the mesoscopic sample during the mechanics testing, and transmit the image data to the control and collection module.

Optionally, the loading module includes a miniature tensile stage and an automatic server;

the mesoscopic sample is arranged on a fixture of the miniature tensile stage; and the automatic server is connected to the miniature tensile stage, is configured to receive a load instruction sent by the control and collection module and control the miniature tensile stage to apply a testing load to the mesoscopic sample, and is further configured to transmit, to the control and collection module, information collected by a load sensor and a displacement sensor that are provided on the miniature tensile stage.

Optionally, the vacuum module includes a vacuum box, a mechanical pump, and a molecular pump; the miniature tensile stage and the mesoscopic sample are both located in the vacuum box;

the mechanical pump and the molecular pump are both connected to the vacuum box;

the mechanical pump is configured to extract air from the vacuum box to reach a first vacuum degree state; and the molecular pump is configured to extract the air from the vacuum box to reach a second vacuum degree state when the vacuum box is in the first vacuum degree state.

Optionally, the system further includes a vacuum measurement module; the vacuum measurement module includes a vacuum gauge and a vacuum degree display unit;

the vacuum gauge is configured to monitor operating parameters of the vacuum module; and the vacuum degree display unit is configured to display monitored operating parameters of the vacuum module.

Optionally, the observation module includes a stereoscopic microscope; the stereoscopic microscope is arranged above an observation window of the vacuum box; and a center of an objective lens of the stereoscopic microscope, a center of the observation window, and a center of the mesoscopic sample are on a straight line.

Optionally, the observation module further includes a ring illuminator; and the ring illuminator is arranged at a periphery of a barrel of the objective lens of the stereoscopic microscope.

Optionally, the vacuum module further includes a heating unit; the heating unit includes a heater, a temperature controller, and a temperature display;
  the heater is arranged below the mesoscopic sample; the temperature controller is connected to the heater; and the temperature display is connected to the temperature controller.

Optionally, the system further includes a cooling module; the cooling module is configured to reduce a temperature around the heater; and the temperature around the heater is a temperature of a space other than regions in contact with the heater and the mesoscopic sample.

Optionally, a thermal insulation ceramic chip is sandwiched between the mesoscopic sample and the fixture of the miniature tensile stage.

The present disclosure provides a mesomechanics testing method integrating heating and observation. The method is implemented on the basis of the mesomechanics testing system integrating heating and observation, and the method includes:
  providing, by a vacuum module, a mesoscopic sample to be tested with a vacuum space for real-time heating and mechanics testing;
  when a vacuum degree in the vacuum space reaches a second vacuum degree state, heating the mesoscopic sample by using a heating unit in the vacuum module;
  when a temperature of the mesoscopic sample reaches a target temperature, applying, by a loading module, a load required by the mechanics testing to the mesoscopic sample, and transmitting mechanics testing data to a control and collection module; and
  collecting, by an observation module, image data of the mesoscopic sample during the mechanics testing, and transmitting the image data to a control and collection module.

According to specific embodiments provided in the present disclosure, the present disclosure disclosures the following technical effects:

The present disclosure provides a mesomechanics testing system and method integrating heating and observation. The testing system synchronously acquires load-displacement data and synchronous image data of the mesoscopic sample at a real-time high temperature. This invention overcomes the defect in the prior art that it is impossible to simultaneously perform real-time heating, mechanical loading and synchronous observation, and can more accurately grasp the continuous dynamic change process of the mesoscopic sample during the mechanical loading process at a real-time high temperature, to reveal the mechanical properties and crack evolution laws of the mesoscopic sample under thermal-mechanical coupling conditions.

BRIEF DESCRIPTION OF THE DRAWINGS

To describe the technical solutions in embodiments of the present disclosure or in the prior art more clearly, the accompanying drawings required in the embodiments are briefly described below. Apparently, the accompanying drawings in the following description show merely some embodiments of the present disclosure, and other drawings can still be derived from these accompanying drawings by those of ordinary skill in the art without creative efforts.

REFERENCE NUMERALS

1. Control and collection module; 2. Automatic server; 3. Miniature tensile stage; 4. Fixture; 5. Zirconia ceramic chip; 6. Rock sample to be tested; 7. Vacuum box; 8. Observation window; 9. Molecular pump adapter port; 10. Molecular pump; 11. Vacuum gauge; 12. Mechanical pump; 13. Corrugated tube; 14. DCU vacuum degree display unit; 15. Stereoscopic microscope; 16. Ring illuminator; 17. Heater; 18. Temperature controller; 19. Temperature display; 20. Small peristaltic pump; 21. Silicone tube; 22. Distilled water; 23. Serve signal transmission system; 24. Load sensor; 25. Displacement sensor; and 26. Flange.

DETAILED DESCRIPTION OF THE EMBODIMENTS

The technical solutions of the embodiments of the present disclosure are clearly and completely described below with reference to the drawings in the embodiments of the present disclosure. Apparently, the described embodiments are merely a part rather than all of the embodiments of the present disclosure. All other examples obtained by a person of ordinary skill in the art based on the examples of the present disclosure without creative efforts shall fall within the protection scope of the present disclosure.

An objective of the present disclosure is to provide a mesomechanics testing system and method integrating heating and observation, which can acquire the mechanical properties of mesoscopic samples to be tested at a real-time high temperature and simultaneously observe the crack extension process of the samples.

In order to make the above objective, features and advantages of the present disclosure clearer and more comprehensible, the present disclosure will be further described in detail below in combination with accompanying drawings and particular implementation modes.

Embodiment 1

Figure 1:
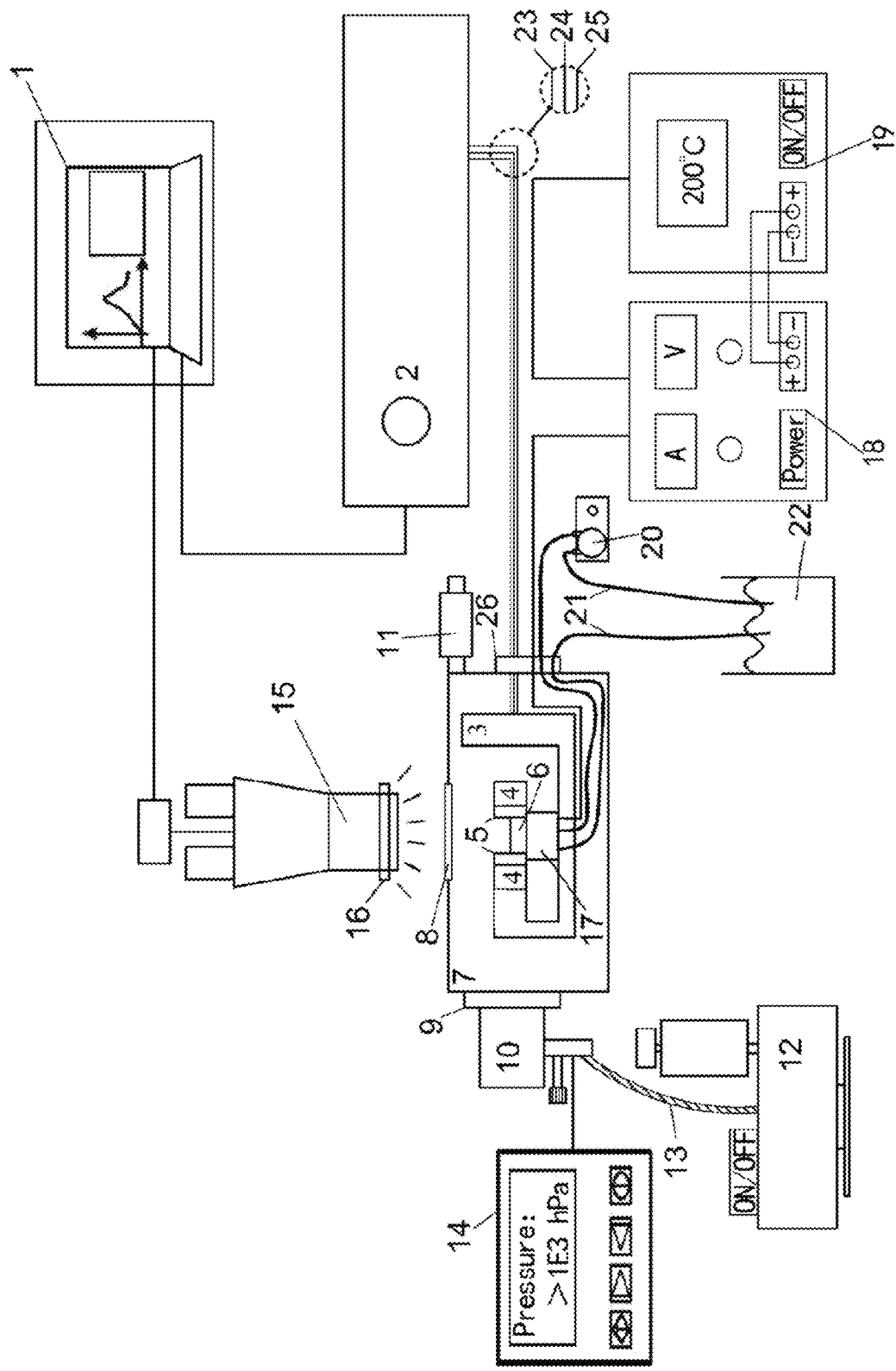
FIG. 1 is a schematic diagram of a mesomechanics testing system integrating heating and observation according to Embodiment 1 of the present disclosure.

As shown in FIG. 1, taking rock mechanics testing as an example, this embodiment provides a mesomechanics testing system integrating heating and observation. The system includes a control and collection module 1, a loading module, a vacuum module, and an observation module. The mesomechanics testing system provided in this embodiment can not only realize mechanics testing of rock, but also mechanical testing of other materials. The rock herein only serves as an example and has no definition effect.

The control and collection module 1 is separately connected to the loading module and the observation module, and is configured to provide a corresponding control instruction to each module and receive related information collected by each module.

The control and collection module 1 controls the loading module and the observation module by transmitting the instructions, such that a sample is loaded under a specified condition, and it is ensured that a sample change process can be synchronously observed. The control and collection module 1 receives mechanical parameter information transmitted back from the loading module and image data transmitted back from the observation module.

The control and collection module 1 includes a control sub-module and a collection sub-module, where the control sub-module controls related parameters of the loading module and the observation module, and the collection sub-module collects mechanical parameters and the image data.

The control and collection module 1 is controlled by a computer, and sends the instructions and stores the information by software which matches the loading module.

The loading module is configured to apply a load required by mechanics testing to a rock sample to be tested 6 in a vacuum space of the vacuum module, and transmit mechanics testing data to the control and collection module 1. The rock sample 6 may be a rock sample at mesoscopic scale, where the mesoscopic scale indicates that the size (such as height, length, diameter, or thickness) of a portion to be tested of the sample is 0.1-10 mm. In addition, it is ensured that the sample 6 can be stably clamped by a fixture 4 of a miniature tensile stage 3 to complete testing.

The loading module includes a miniature tensile stage 3 and an automatic server 2.

The rock sample 6 is arranged on the fixture 4 of the miniature tensile stage 3. The miniature tensile stage 3 can load different rock material samples in different forms by replacing the fixture 4, to quickly and accurately test the tensile, compression, bending, creep, fatigue and other properties of the materials.

A thermal insulation ceramic chip is sandwiched between the rock sample 6 and the fixture 4 of the miniature tensile stage 3. For example, a zirconia ceramic chip 5 may be placed between the fixture 4 of the miniature tensile stage 3 and the sample for thermal insulation, to further prevent the heat of the sample from being transferred to the instrument.

The automatic server 2 is connected to the miniature tensile stage 3, is configured to receive a load instruction sent by the control and collection module 1 and control the miniature tensile stage 3 to apply a testing load to the rock sample 6, and is further configured to transmit, to the control and collection module 1, information collected by a load sensor 24 and a displacement sensor 25 that are provided on the miniature tensile stage 3. The miniature tensile stage transmits load data and displacement data to the automatic server through data transmission lines and then transmits same to the control and collection module. The data transmission lines between the miniature tensile stage and the automatic server pass through the vacuum box of the vacuum module.

Different loading behaviors can be implemented through a load change instruction and by replacing the fixture 4.

The vacuum module is configured to provide the rock sample 6 with a vacuum space for real-time heating and mechanics testing.

The vacuum module includes a vacuum box 7, a mechanical pump 12, and a molecular pump 10. The miniature tensile stage 3, the heater 17 and the rock sample 6 are all located in the vacuum box 7. The vacuum box 7 is sealed by using a sealing strip and vacuum silicone grease to avoid the situation where due to poor sealing performance, the mechanical pump 12 and the molecular pump 10 cannot extract the gas inside the box body to reach a target vacuum degree.

The mechanical pump 12 and the molecular pump 10 are both connected to the vacuum box 7, and both extract the gas inside the vacuum box 7 to reach a high vacuum state for service.

The mechanical pump 12 is configured to extract air from the vacuum box 7 to reach a first vacuum degree state.

The molecular pump 10 is configured to extract the air from the vacuum box 7 to reach a second vacuum degree state when the vacuum box 7 is in the first vacuum degree state.

Figure 2:
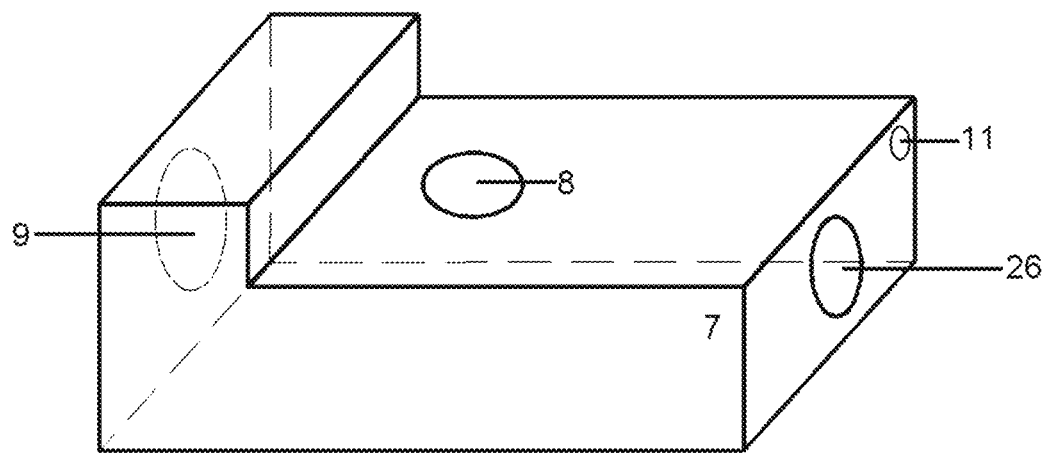
FIG. 2 is a schematic structural diagram of a vacuum box according to Embodiment 1 of the present disclosure.
Figure 3:
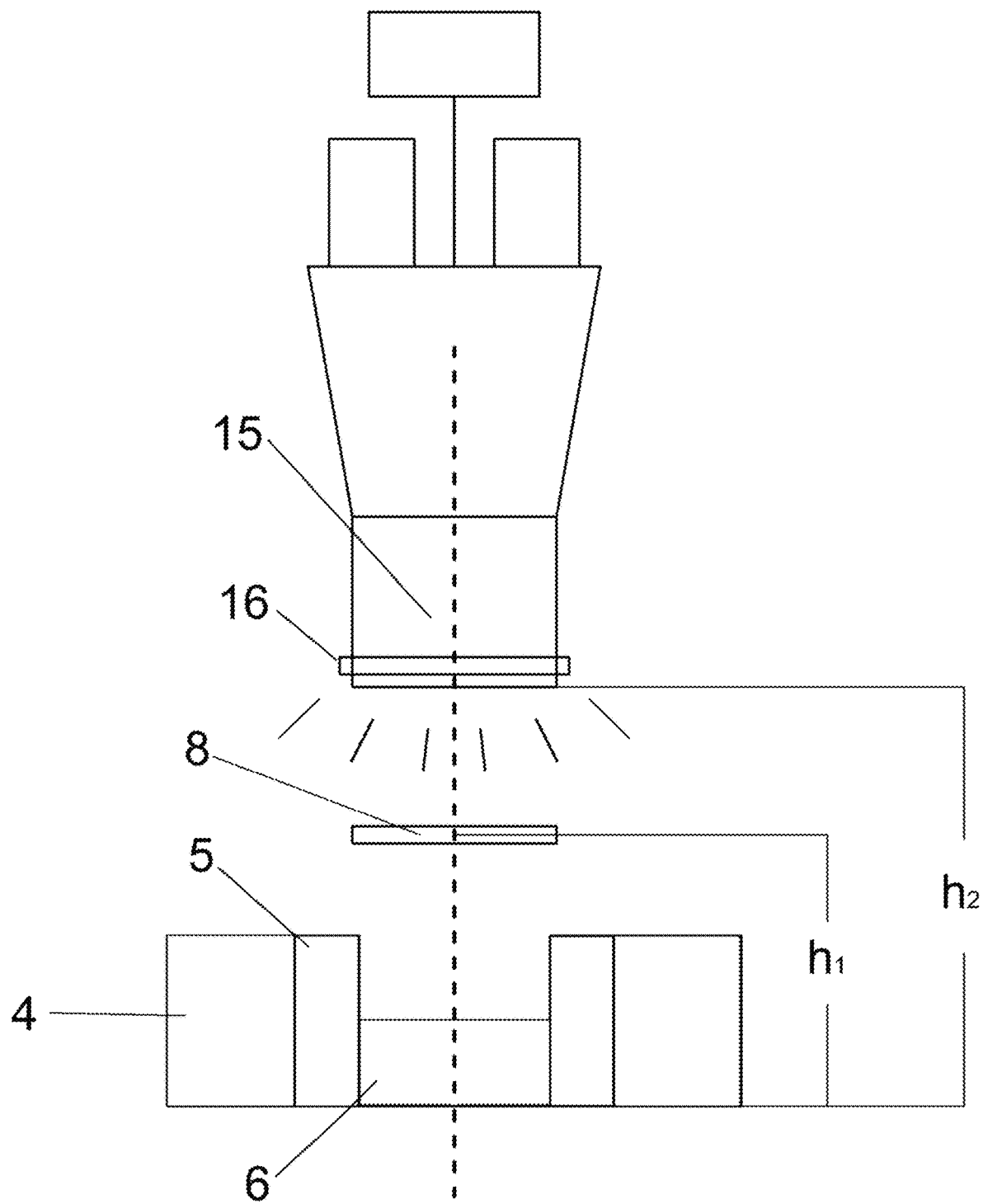
FIG. 3 is a schematic diagram of a positional relationship among a stereoscopic microscope, an observation window, and a miniature tensile stage according to Embodiment 1 of the present disclosure.

As shown in FIG. 2, the vacuum box 7 needs to ensure:
(1) to leave an enough space inside for placing the miniature tensile stage 3;
(2) to leave an interface for mounting a flange 26, where the flange ensures that a servo signal transmission system 23, a load sensor 24 and a displacement sensor 25 are connected to the miniature tensile stage 3 inside the box body and the automatic server 2 outside the box body;
(3) to leave an interface for mounting a flange 26, where the flange ensures that the heater 17 inside the box body can be connected to a temperature controller 18 and a cooling module outside the box body;
(4) to leave a molecular pump adapter port 9 which is connected to the molecular pump 10;
(5) to leave an observation window 8;
(6) to leave an interface for connecting a vacuum gauge 11;
(7) to ensure, after the overall box body (including the observation window 8) is sealed, that the external atmosphere can be borne at high internal vacuum; and
(8) that the position of the observation window 8 needs to ensure that a center of the rock sample 6, a center of the observation window 8 and a center of an objective lens of the stereoscopic microscope 15 are on a straight line; that the height of the observation window 8 needs to ensure that the distance from the observation window 8 to the rock sample 6 is less than the focal distance required by the stereoscopic microscope 15 to observe the rock sample 6, where as shown in FIG. 3, $h_1$ is the distance from the observation window 8 to the bottom of the rock sample 6, and $h_2$ is the distance from the bottommost end of the objective lens of the stereoscopic microscope 15 to the bottom of the rock sample 6.

The system further includes a vacuum measurement module; the vacuum measurement module includes a vacuum gauge 11 and a DCU vacuum degree display unit 14.

The vacuum gauge 11 is configured to monitor operating parameters of the vacuum module, such as monitoring in real time the vacuum degree inside the vacuum box 7 and the operating state (rotating speed, working current and the like) of the molecular pump 10 or the operating state of the mechanical pump 12, etc.

The DCU vacuum degree display unit 14 is configured to display monitored operating parameters of the vacuum module.

The observation module is configured to collect the image data of the rock sample 6 in the mechanics testing process, and transmit the image data to the control and collection module 1.

The observation module includes a stereoscopic microscope 15; the stereoscopic microscope 15 is arranged above the observation window 8 of the vacuum box 7, is connected to the control and collection module 1, and is configured to observe the image data of the sample in the loading module in the loading process, which is recorded and stored by the control and collection module 1. The center of the objective lens of the stereoscopic microscope 15, the center of the observation window 8, and the center of the rock sample 6 are on a straight line.

The observation module further includes a ring illuminator 16; and the ring illuminator 16 is arranged at a periphery of a barrel of the objective lens of the stereoscopic microscope 15.

The stereoscopic microscope 15 captures the image data (including morphological features of the sample before loading, changes of the sample during the loading process, and morphological features of the sample after failure) of the rock sample 6 on the miniature tensile stage 3 inside the vacuum box 7 through the observation window 8. The ring illuminator 16 mounted at a periphery of the barrel of the objective lens of the stereoscopic microscope 15 is configured to reduce the shadow of the sample, such that light is uniformly scattered on the rock sample 6. The captured image data is stored by the control and collection module 1.

To conveniently provide real-time heating conditions to the rock sample 6 in the mechanics testing process, the vacuum module further includes a heating unit; the heating unit includes a heater 17, a temperature controller 18, and a temperature display 19.

The heater 17 is arranged below the rock sample 6; the temperature controller 18 is connected to the heater 17, and performs heating and cooling by controlling a voltage and a current; and the temperature display 19 is connected to the temperature controller 18, and displays the temperature at the current voltage and current.

The heater 17 is connected to the loading module, is located in the vacuum box 7, and directly performs contact heating on the sample. The heater 17 is connected to a temperature controller 18 and a temperature display 19 outside the vacuum box 7 through flanges 26. The temperature controller 18 and the temperature display 19 are configured to regulate and monitor the temperature of the heater 17.

The system further includes a cooling module; the cooling module is configured to reduce a temperature around the heater 17; and the temperature around the heater 17 is a temperature of a space other than regions in contact with the heater 17 and the rock sample 6.

The cooling module is connected to distilled water 22 and the heater 17 through a silicone tube 21, takes away the heat around the heater 17, and prevents the heat accumulated by the heater 17 from being transferred to the instrument to cause damage. The cooling module may perform water circulation by using a small peristaltic pump 20 to avoid the situation where due to insufficient water voltage, the heat of the heater 17 cannot be taken away in time.

The solution of this embodiment can perform real-time heating, mechanics testing and synchronous observation on tiny rock samples, and effectively acquire the mechanical properties and crack extension laws of the rock at a real-time high temperature.

Figure 4:
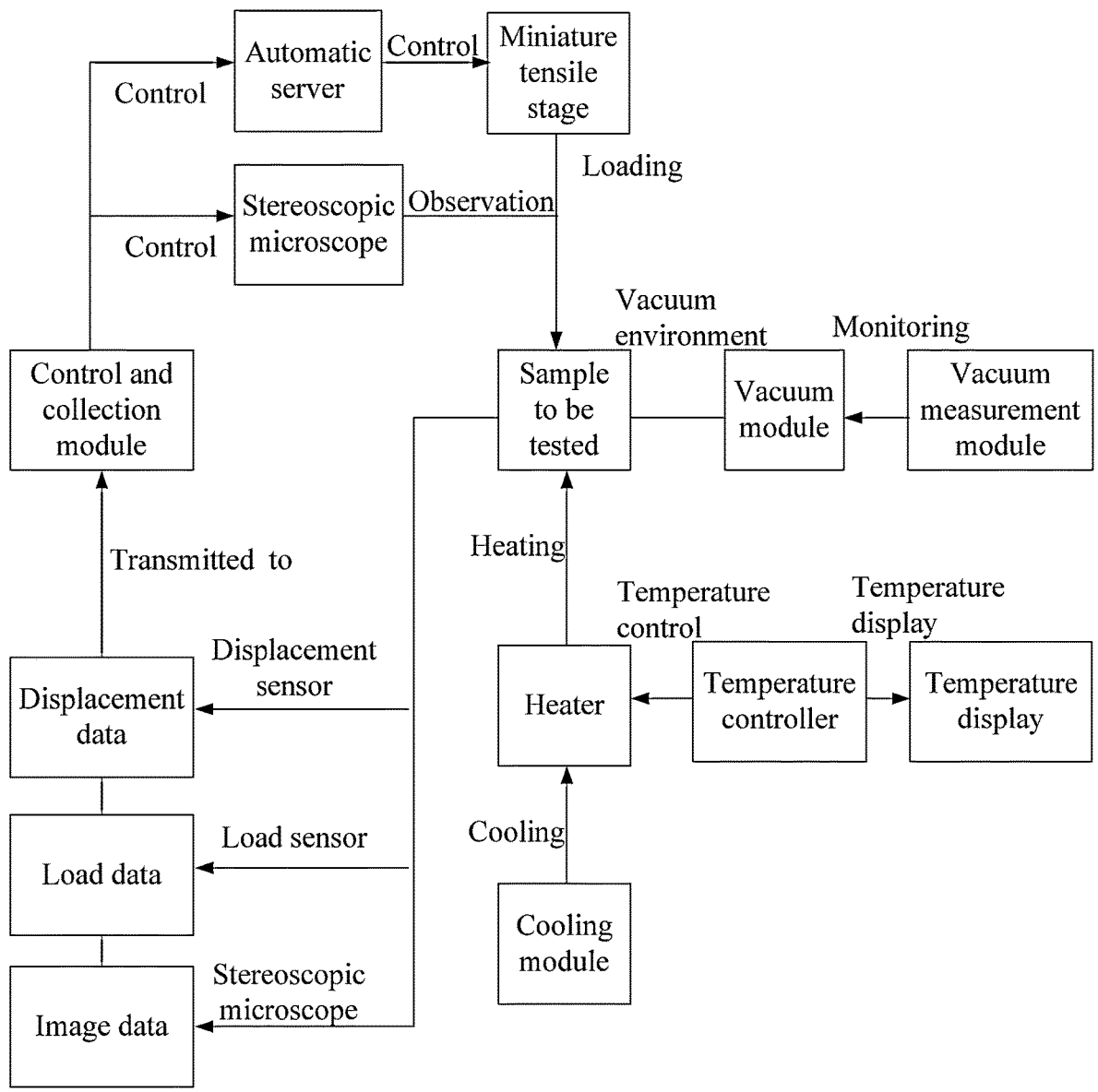
FIG. 4 is a schematic diagram of the principle of a testing system according to Embodiment 1 of the present disclosure.

In view of the main principle of the testing system shown in FIG. 4, the implementation process of applying the testing system of this embodiment to perform real-time high-temperature mechanical property testing and synchronous observation is specifically described:

Step S100, mount the rock sample 6 on the miniature tensile stage 3, make the rock sample 6 in direct contact with the heater 17, set parameters of the loading module and the observation module by the control and collection module 1 to reach test requirements, and then seal the vacuum box 7.

Step S200, turn on the mechanical pump 12, extract the air inside the vacuum box 7 to an air pressure at which the molecular pump 10 is suitable to operate, then turn on the molecular pump 10, observe the DCU vacuum degree display unit 14 until the vacuum degree inside the box body meets experimental requirements.

Step S300, turn on the cooling module, turn on the temperature display 19 to set the target temperature, turn on the temperature controller 18 to regulate the voltage and current for real-time heating, observe the temperature displayed by the temperature display 19, and keep a constant temperature after the temperature is regulated to a temperature specified by the experimental requirements.

Step S400, after the constant temperature lasts for a period of time, turn on the loading module and the observation module by the control and collection module 1, perform a mechanical loading test on the rock sample, and after the mechanical loading test is finished, export the collected mechanics testing data and image data by the control and collection module 1.

Step S500, after the mechanical loading test is finished, rotatably regulating the voltage and current of the temperature controller 18 to zero, after the temperature displayed by the temperature display 19 is reduced to room temperature, turn off the heating unit, and turn off the molecular pump 10, wait for the reduction of the rotating speed of the molecular pump 10, then turn off the mechanical pump 12 until the air pressure in the vacuum box 7 is increased to the atmospheric pressure, open the vacuum box 7, unload and take out the broken rock sample, and close the vacuum box 7.

Step S600, take out the broken sample, perform observation by the observation module, and calculate the roughness of broken surfaces of the sample.

Step S700, turn off each module and reset to an original position after the test ends.

Taking shale loading at 200° C. as an example, the specific operation steps are as follows:

(1) sample mounting: mount a shale sample having a diameter of 3 mm and a height of 6 mm on the heater 17, at a preset loading rate of 0.036 mm/min, where the size of the sample is at mesoscopic scale, and the shape of the sample and the loading rate can be regulated according to a testing scheme; then seal the vacuum box 7; and regulate the position and focal distance of the stereoscopic microscope 15, to ensure that the observation module can normally observe the sample and perform recording by camera.

(2) vacuum extraction: start the DCU vacuum degree display unit 14, transfer to the vacuum degree display interface, and observe the vacuum degree inside the box body in real time; and start the mechanical pump 12, and start the molecular pump 10 after the vacuum degree inside the vacuum box 7 is reduced to 1 hPa.

(3) heating: when a vacuum degree inside the box body reaches $1 \times 10^{-5}$ hPa, turn on the small peristaltic pump 20, after the silicone tube 21 is filled with the distilled water 22, turn on the temperature display 19 and the temperature controller 18 in sequence, preset a temperature for the temperature display 19, regulate the voltage and current by the temperature controller 18 until the temperature reaches a specified temperature 200° C., and then keep the temperature for 0.5-1 h; and need to slowly regulate the temperature controller 18, where the heating rate does not exceed 50° C./min, to avoid the damage of components due to too fast heating.

(4) mechanics testing: after the above steps are completed, turn on the observation module and the loading module, synchronously collect the displacement and load information and the image data of the sample during the loading process until the sample is damaged, and stop loading and recording when the load is obviously reduced (or stop loading according to other testing requirements).

(5) room temperature recovery: rotatably regulate the current and voltage of the temperature controller 18 to zero, and turn off the heating unit after the temperature displayed by the temperature display 19 is reduced to room temperature; turn off the molecular pump 10, regulate the DCU vacuum degree display unit 14 to the rotating speed display interface of the molecular pump 10, and turn off the mechanical pump 12 after the rotating speed is reduced to 300 Hz; and regulate the DCU vacuum degree display unit 14 to the vacuum degree display interface, observe the air pressure inside the box body until it increases to one atmospheric pressure, open the vacuum box 7.

(6) sample unloading: turn off the cooling module after it is ensured that the instrument is completely cooled to room temperature; control the miniature tensile stage 3 to unload the sample by the control and collection module 1, take out the broken rock by tweezers, and turn off the loading module; and place the taken-out broken rock under the stereoscopic microscope 15 for observation to acquire roughness information of the broken surfaces.

(7) testing completion: turn off all the modules, and reset to the original state.

Embodiment 2

This embodiment provides a mesomechanics testing method integrating heating and observation. The method is implemented on the basis of the mesomechanics testing system integrating heating and observation provided by Embodiment 1, and the method includes:

provide, by a vacuum module, a rock sample to be tested 6 with a vacuum space for real-time heating and mechanics testing;

when a vacuum degree in a vacuum space reaches a second vacuum degree state, heat the rock sample 6 by using a heating unit;

when a temperature of the rock sample 6 reaches a target temperature, apply, by a loading module, a load required by the mechanics testing to the rock sample 6, and transmit mechanics testing data to a control and collection module; and collect, by an observation module, image data of the rock sample 6 in the mechanics testing process, and transmit the image data to the control and collection module.

Each embodiment in the description is described in a progressive mode, each embodiment focuses on differences from other embodiments, and references can be made to each other for the same and similar parts between embodiments.

Specific examples are used herein for illustration of the principles and embodiments of the present disclosure. The description of the foregoing embodiments is used to help understand the method of the present disclosure and the core principles thereof. In addition, those of ordinary skill in the art can make various modifications in terms of specific embodiments and scope of application in accordance with the teachings of the present disclosure. In conclusion, the content of the description shall not be construed as limitations to the present disclosure.

What is claimed is:

1. A mesomechanics testing system integrating heating and observation, comprising a control and collection module, a loading module, a vacuum module, and an observation module; wherein the loading module and the observation module are both connected to the control and collection module;

the vacuum module is configured to provide a mesoscopic sample to be tested with a vacuum space for real-time heating and mechanics testing; the mesoscopic sample is a rock sample at mesoscopic scale; the mesoscopic scale indicates that a size of a portion to be tested of the sample is 0.1-10 mm; the vacuum module comprises a vacuum box;

the loading module is configured to apply a load required by the mechanics testing to the mesoscopic sample in the vacuum space, and transmit mechanics testing data to the control and collection module; and the observation module is configured to collect image data of the mesoscopic sample during the mechanics testing, and transmit the image data to the control and collection module; wherein the observation module comprises a stereoscopic microscope and a ring illuminator; the stereoscopic microscope is arranged above an observation window of the vacuum box; and a center of an objective lens of the stereoscopic microscope, a center of the observation window, and a center of the mesoscopic sample are on a straight line; and the ring illuminator is arranged at a periphery of a barrel of the objective lens of the stereoscopic microscope the vacuum module further comprises a heating unit; the heating unit comprises a heater, a temperature controller, and a temperature display; the heater is arranged below the mesoscopic sample; the temperature controller is connected to the heater; and the temperature display is connected to the temperature controller; and a thermal insulation ceramic chip is sandwiched between the mesoscopic sample and a fixture of a miniature tensile stage.

2. The system according to claim 1, wherein the loading module comprises a miniature tensile stage and an automatic server;

the mesoscopic sample is arranged on a fixture of the miniature tensile stage; and the automatic server is connected to the miniature tensile stage, is configured to receive a load instruction sent by the control and collection module and control the miniature tensile stage to apply a testing load to the mesoscopic sample, and is further configured to transmit, to the control and collection module, information collected by a load sensor and a displacement sensor that are provided on the miniature tensile stage.

3. The system according to claim 2, wherein the vacuum module further comprises a mechanical pump and a molecular pump; the miniature tensile stage and the mesoscopic sample are both located in the vacuum box;

the mechanical pump and the molecular pump are both connected to the vacuum box;

the mechanical pump is configured to extract air from the vacuum box to reach a first vacuum degree state; and the molecular pump is configured to extract the air from the vacuum box to reach a second vacuum degree state when the vacuum box is in the first vacuum degree state.

4. The system according to claim 3, further comprising a vacuum measurement module, wherein the vacuum measurement module comprises a vacuum gauge and a vacuum degree display unit;

the vacuum gauge is configured to monitor operating parameters of the vacuum module; and the vacuum degree display unit is configured to display monitored operating parameters of the vacuum module.

5. The system according to claim 1, wherein the system further comprises a cooling module; the cooling module is configured to reduce a temperature around the heater; and the temperature around the heater is a temperature of a space other than regions in contact with the heater and the mesoscopic sample.

6. A mesomechanics testing method integrating heating and observation, wherein the method is implemented on the basis of the mesomechanics testing system integrating heating and observation according to claim 1, and the method comprises:

providing, by a vacuum module, a mesoscopic sample to be tested with a vacuum space for real-time heating and mechanics testing;

when a vacuum degree in the vacuum space reaches a second vacuum degree state, heating the mesoscopic sample by using a heating unit in the vacuum module;

when a temperature of the mesoscopic sample reaches a target temperature, applying, by a loading module, a load required by the mechanics testing to the mesoscopic sample, and transmitting mechanics testing data to a control and collection module; and collecting, by an observation module, image data of the mesoscopic sample during the mechanics testing, and transmitting the image data to a control and collection module.

7. The mesomechanics testing method integrating heating and observation according to claim 6, wherein the loading module comprises a miniature tensile stage and an automatic server;

the mesoscopic sample is arranged on a fixture of the miniature tensile stage; and the automatic server is connected to the miniature tensile stage, is configured to receive a load instruction sent by the control and collection module and control the miniature tensile stage to apply a testing load to the mesoscopic sample, and is further configured to transmit, to the control and collection module, information collected by a load sensor and a displacement sensor that are provided on the miniature tensile stage.

8. The mesomechanics testing method integrating heating and observation according to claim 7, wherein the vacuum module further comprises a mechanical pump and a molecular pump; the miniature tensile stage and the mesoscopic sample are both located in the vacuum box;

the mechanical pump and the molecular pump are both connected to the vacuum box;

the mechanical pump is configured to extract air from the vacuum box to reach a first vacuum degree state; and the molecular pump is configured to extract the air from the vacuum box to reach a second vacuum degree state when the vacuum box is in the first vacuum degree state.

9. The mesomechanics testing method integrating heating and observation according to claim 8, further comprising a vacuum measurement module, wherein the vacuum measurement module comprises a vacuum gauge and a vacuum degree display unit;

the vacuum gauge is configured to monitor operating parameters of the vacuum module; and the vacuum degree display unit is configured to display monitored operating parameters of the vacuum module.

10. The mesomechanics testing method integrating heating and observation according to claim 6, wherein the system further comprises a cooling module; the cooling module is configured to reduce a temperature around the heater; and the temperature around the heater is a temperature of a space other than regions in contact with the heater and the mesoscopic sample.

* * * * *